United States Patent
Dake et al.

(10) Patent No.: US 10,393,661 B2
(45) Date of Patent: Aug. 27, 2019

(54) STRUCTURED ILLUMINATION MICROSCOPIC DEVICE AND STRUCTURED ILLUMINATION OBSERVATION METHOD

(71) Applicant: NIKON CORPORATION, Tokyo (JP)

(72) Inventors: Fumihiro Dake, Kawasaki (JP); Hiroki Yazawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 99 days.

(21) Appl. No.: 15/298,864

(22) Filed: Oct. 20, 2016

(65) Prior Publication Data

US 2017/0038300 A1 Feb. 9, 2017

Related U.S. Application Data

(63) Continuation of application No. PCT/JP2015/002192, filed on Apr. 22, 2015.

(30) Foreign Application Priority Data

Apr. 25, 2014 (JP) .................. 2014-091456

(51) Int. Cl.
*G01N 21/64* (2006.01)
*G02B 21/06* (2006.01)
(Continued)

(52) U.S. Cl.
CPC ..... *G01N 21/6458* (2013.01); *G01N 21/6428* (2013.01); *G02B 21/0032* (2013.01);
(Continued)

(58) Field of Classification Search
None
See application file for complete search history.

(56) References Cited

U.S. PATENT DOCUMENTS

| RE38,307 E | 11/2003 | Gustafsson et al. |
| 2002/0063220 A1* | 5/2002 | Engelhardt ............ B82Y 15/00 250/458.1 |

(Continued)

FOREIGN PATENT DOCUMENTS

| JP | 2010-506203 A | 2/2010 |
| WO | 2006/109448 A1 | 10/2006 |

(Continued)

OTHER PUBLICATIONS

Jul. 28, 2015 International Search Report issued in International Patent Application No. PCT/JP2015/002192.

(Continued)

*Primary Examiner* — Edwin C Gunberg
(74) *Attorney, Agent, or Firm* — Oliff PLC

(57) ABSTRACT

A structured illumination microscopic device includes a first spatial modulation unit spatially modulating a fluorescent sample using an excitation light having a sinusoidal illumination distribution of a spatial frequency K and having an optical frequency $\omega_1$ for shifting a fluorescent substance to an excitation level; a second spatial modulation unit spatially modulating the fluorescent sample using a stimulation light having a sinusoidal illumination distribution of a spatial frequency K and having an optical frequency $\omega_2$ for shifting the excited fluorescent substance to a base level; and an imaging unit obtaining, as a modulated image, an image of the fluorescent sample with spontaneously emitted light generated at the fluorescent sample in accordance with the excitation light and the stimulation light.

6 Claims, 7 Drawing Sheets

(51) Int. Cl.
  *G02B 21/36* (2006.01)
  *G02B 21/16* (2006.01)
  *G02B 21/00* (2006.01)

(52) U.S. Cl.
  CPC ..... *G02B 21/0056* (2013.01); *G02B 21/0072* (2013.01); *G02B 21/06* (2013.01); *G02B 21/16* (2013.01); *G02B 21/36* (2013.01); *G02B 21/367* (2013.01); *G01N 2021/6439* (2013.01); *G01N 2201/0697* (2013.01); *G01N 2201/06113* (2013.01); *G01N 2201/12* (2013.01)

(56) References Cited

U.S. PATENT DOCUMENTS

| | | | |
|---|---|---|---|
| 2009/0046164 A1* | 2/2009 | Shroff | A61B 3/12 348/222.1 |
| 2009/0250632 A1 | 10/2009 | Kempe et al. | |
| 2010/0141750 A1 | 6/2010 | Osawa et al. | |
| 2015/0185463 A1 | 7/2015 | Ohki et al. | |
| 2015/0211997 A1 | 7/2015 | Dake | |

FOREIGN PATENT DOCUMENTS

| | | |
|---|---|---|
| WO | 2014/013720 A1 | 1/2014 |
| WO | 2014/057998 A1 | 4/2014 |

OTHER PUBLICATIONS

Jul. 28, 2015 Written Opinion issued in International Patent Application No. PCT/JP2015/002192.

Oct. 25, 2016 International Preliminary Report on Patentability issued in PCT/JP2015/002192.

Kner, Peter et al., "Super-resolution video microscopy of live cells by structured illumination", Nature Methods, May 2009, vol. 6, No. 5, pp. 339-342.

Zhang, Han et al., "Nonlinear structured illumination microscopy by surface plasmon enhanced stimulated emission depletion", Optics Express, Nov. 18, 2011, vol. 19, No. 24, pp. 24783-24794.

Zhang, Han et al., "Nonlinear Structured Illumination Microscopy with Surface Plasmon Resonance Enhanced Stimulated Emission Depletion", Proc. of SPIE, Feb. 22, 2013, vol. 8590, pp. 859011-1-859011-6.

Sep. 5, 2017 Office Action issued in Japanese Patent Application No. 2016-514721.

* cited by examiner $I_{ex} = I_e(1 + \cos Kx)$ $I_{st} = I_s(1 + \cos Kx + \phi_s)$ $I_{ex}$ $I_{sp} \propto A/(A + B \cdot I_{st}) \cdot I_{ex}$

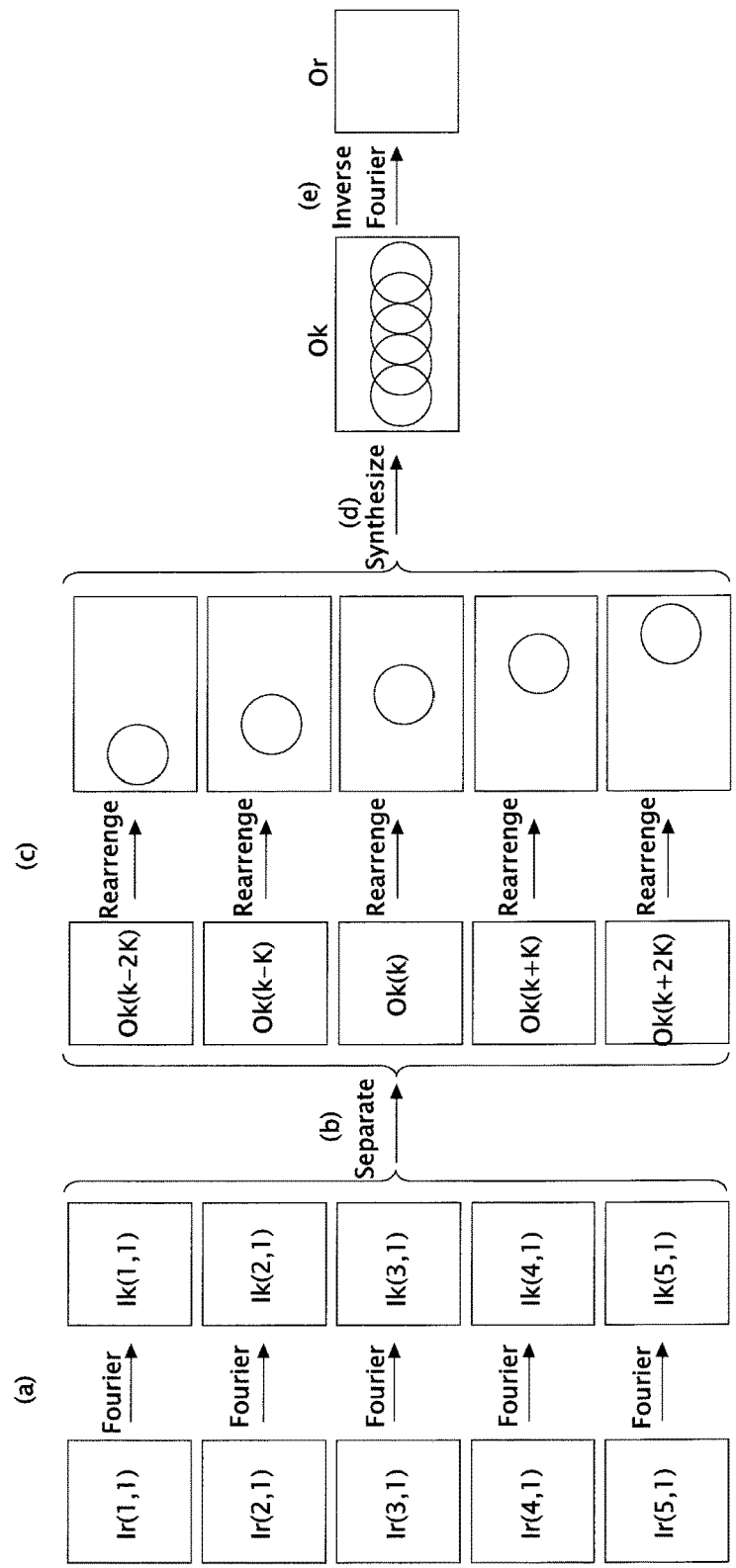

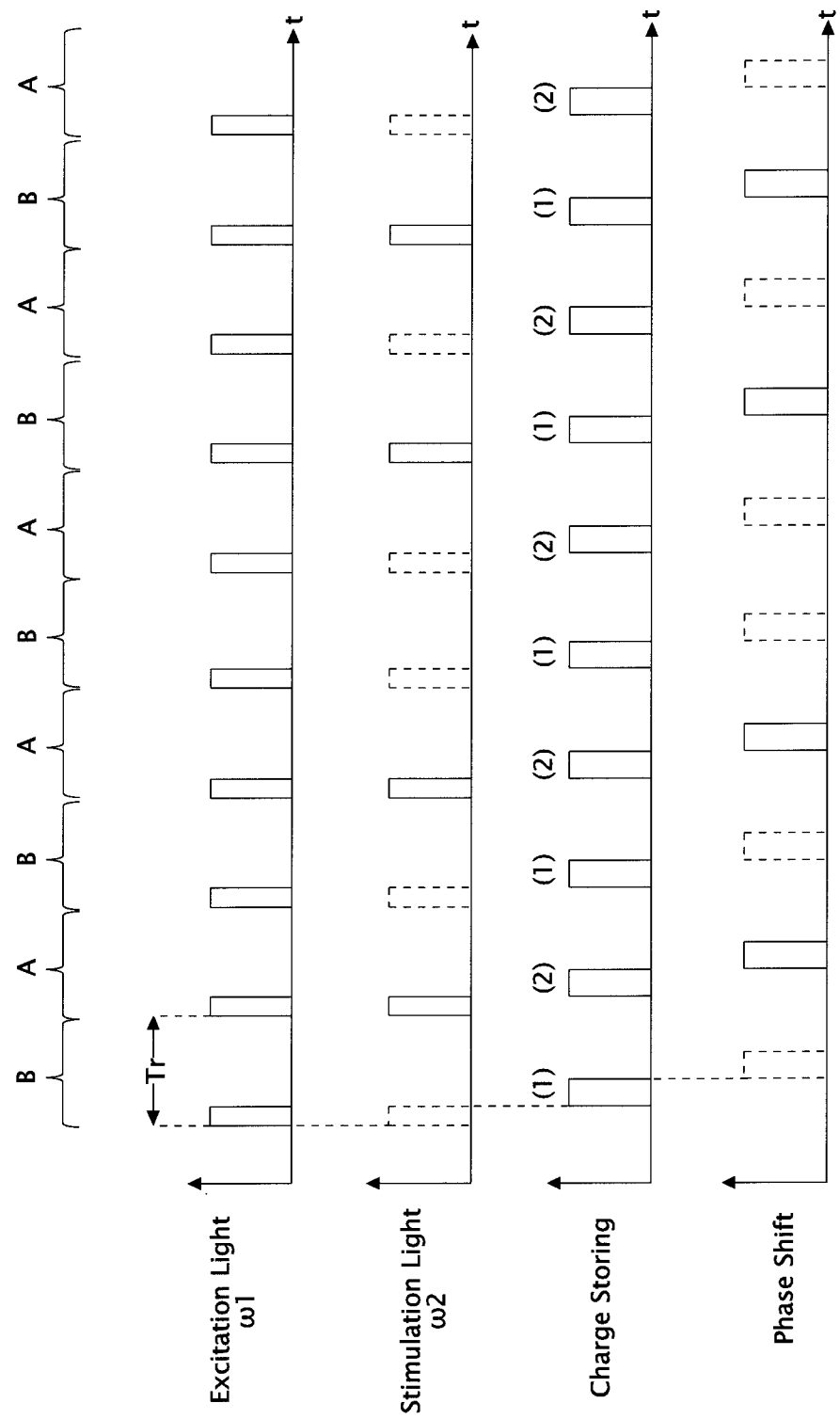

STRUCTURED ILLUMINATION MICROSCOPIC DEVICE AND STRUCTURED ILLUMINATION OBSERVATION METHOD

CROSS-REFERENCE TO RELATED APPLICATION

This application is a continuation application of International Application PCT/JP2015/002192, filed Apr. 22, 2015, designating the U.S., and claims the benefit of priority from Japanese Patent Application No. 2014-091456, filed on Apr. 25, 2014, the entire contents of which are incorporated herein by reference.

BACKGROUND

1. Field

The present application relates to a structured illumination microscopic device and a structured illumination observation method.

2. Description of the Related Art

It is a fluorescence microscope that is utilized as a principal microtechnique in the field of bioscience, particularly molecular biology. In recent years in particular, a super-resolution microscope that achieves a spatial resolution of 100 nm or less appears, which achieves a further contribution to the field of bioscience.

There is a SIM (Structured Illumination Microscopy) as a widely utilized super-resolution microscope (see Specification of U.S. Pat. No. RE 38,307 and the like). The SIM is a microscopy that at the maximum doubles a resolution by spatially modulating a sample using an excitation light having a grating pattern.

However, although the resolution that can be achieved by the current SIM is 100 nm or so, the size of a cell organelle being an observation object is 50 nm, and thus a further improvement in resolution is required.

Incidentally, a NSIM (Nonlinear Structured Illumination Microscopy) saturates excitation by increasing illumination of an excitation light to saturate an amount of fluorescence emitted from a fluorescent sample and superimposes high spatial frequency components on appearance on an illumination pattern, thereby achieving a high resolution. However, there is a problem that intensity of the excitation light is increased, and thereby damage to a biological sample increases.

The present application provides a structured illumination microscopic device and a structured illumination observation method capable of achieving a high resolution (for example, a resolution higher than that of a SIM) without significantly increasing illumination of an excitation light.

SUMMARY

One aspect of a structured illumination microscopic device exemplifying the present embodiment includes a first spatial modulation unit that spatially modulates a fluorescent sample using an excitation light having a sinusoidal illumination distribution of a spatial frequency K and having an optical frequency $\omega_1$ for shifting a fluorescent substance to an excitation level; a second spatial modulation unit that spatially modulates the fluorescent sample using a stimulation light having a sinusoidal illumination distribution of a spatial frequency K and having an optical frequency $\omega_2$ for shifting the fluorescent substance exciting to a base level; and an imaging unit that obtains, as a modulated image, an image of the fluorescent sample with spontaneously emitted light generated at the fluorescent sample in accordance with the excitation light and the stimulation light.

One aspect of a structured illumination observation method exemplifying the present embodiment includes spatially modulating a fluorescent sample using an excitation light having a sinusoidal illumination distribution of a spatial frequency K and having an optical frequency $\omega_1$ for shifting a fluorescent substance to an excitation level; spatially modulating the fluorescent sample using a stimulation light having a sinusoidal illumination distribution of a spatial frequency K and having an optical frequency $\omega_2$ for shifting the fluorescent substance exciting to a base level; and obtaining, as a modulated image, an image of the fluorescent sample with spontaneously emitted light generated at the fluorescent sample in accordance with the excitation light and the stimulation light.

According to the present application, there are realized a structured illumination microscopic device and a structured illumination observation method capable of achieving a high resolution without significantly increasing illumination of an excitation light.

BRIEF DESCRIPTION OF THE DRAWINGS

FIG. 6 is a diagram explaining a demodulating calculation when a phase number $N_{max}=5$ and a direction number $M_{max}=1$ are satisfied.

FIG. 9 is a timing chart of a ST-SIM of a second embodiment.

DETAILED DESCRIPTION OF THE EMBODIMENTS

First Embodiment

Hereinafter, there will be explained a stimulated emission-structured illumination microscopy (ST-SIM: Stimulated Emission-Structured Illumination Microscopy) as a first embodiment of the present invention. Here, a case where a stimulated emission process is applied to a SIM in which structured illumination is realized by two-beam interference, namely a 2D-SIM (Two-Dimensional Structured Illumination Microscopy), is imagined.

Figure 1:
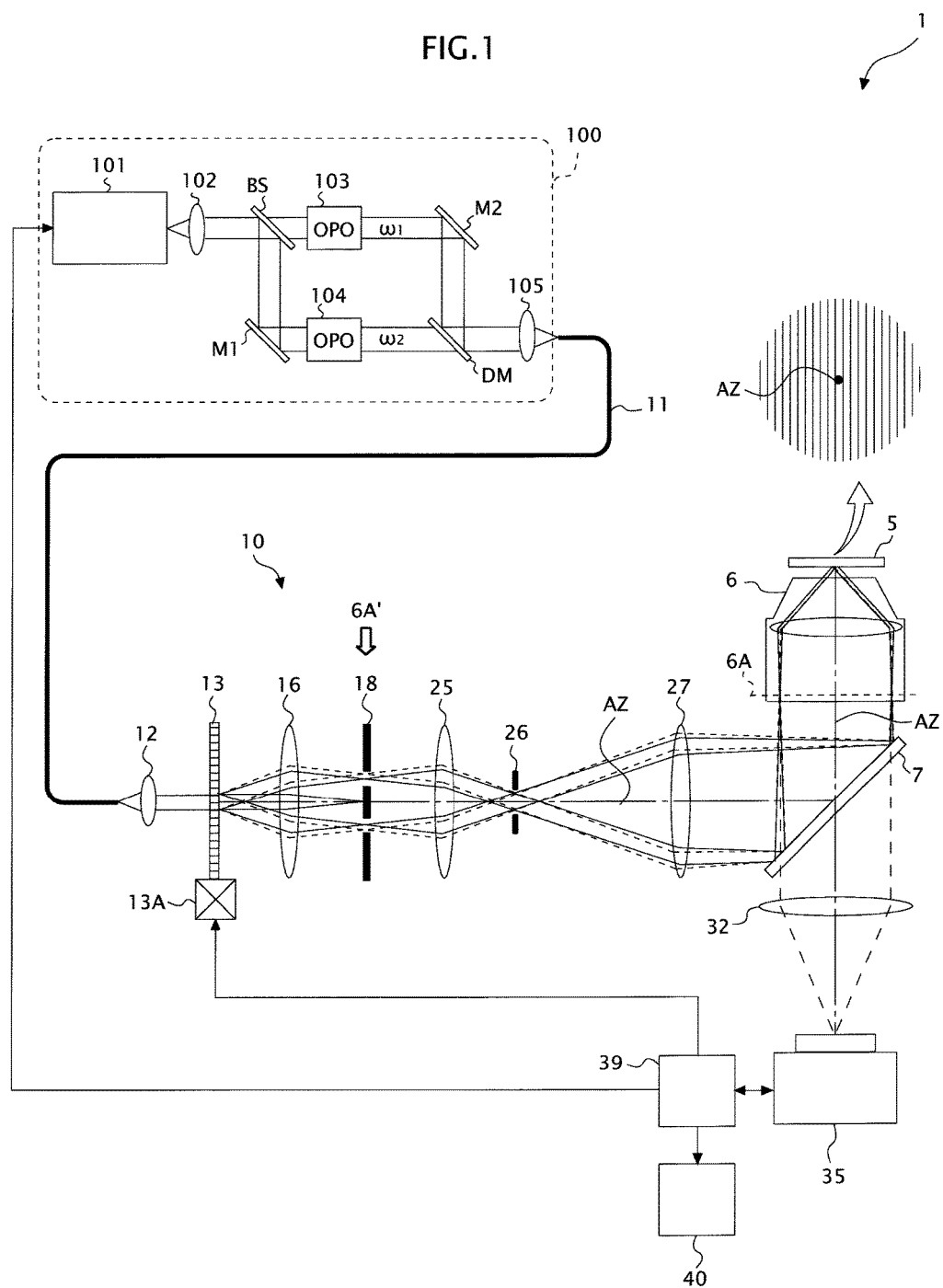
FIG. 1 is a configuration diagram of a ST-SIM of a first embodiment.

First, a configuration of the ST-SIM is explained with reference to FIG. 1. As illustrated in FIG. 1, there are provided, in a ST-SIM 1, a laser unit 100, an optical fiber 11, an illuminating optical system 10, a second objective lens 32, an imaging sensor 35, a controlling device 39, and an image storage-calculation device 40.

In the laser unit 100, there are disposed a pulsed laser light source 101, a lens 102, a beam splitter BS, optical parametric oscillators 103 and 104, mirrors M1 and M2, a dichroic mirror DM, a lens 105, and the like. In the illuminating optical system 10, there are disposed a collector lens 12, a phase type diffraction grating 13, a mechanism 13A, a collecting lens 16, a 0th-order light blocking mask 18, a lens 25, a field stop 26, a field lens 27, a dichroic mirror 7, an objective lens 6, and a sample 5.

A light source of the laser unit 100 is the pulsed laser light source 101. A repetition frequency fr of pulse oscillation by means of the pulsed laser light source 101 is 80 MHz, for example. Note that the light source of the laser unit 100 is not the pulsed laser light source, but may be a CW laser light source (CW: Continuous wave), but the pulsed laser light source is imagined here.

A pulsed laser light exited from the pulsed laser light source 101 is turned into a collimated light flux having a large diameter by the lens 102 to be incident on the beam splitter BS. The pulsed laser light incident on the beam splitter BS is split into a pulsed laser light that transmits through the beam splitter BS and a pulsed laser light to be reflected by the beam splitter BS, and the pulsed laser light transmitted through the beam splitter BS is incident on the optical parametric oscillator 103. The pulsed laser light reflected by the beam splitter BS is incident on the mirror M1, and reflected by the mirror M1 to be incident on the optical parametric oscillator 104.

The optical parametric oscillator 103 converts an optical frequency of the incident pulsed laser light into $\omega_1$, and the optical parametric oscillator 104 converts an optical frequency of the incident pulsed laser light into $\omega_2$. Here, the relation between the optical frequencies $\omega_1$ and $\omega_2$ is set to $\omega_2 < \omega_1$.

The pulsed laser light of the optical frequency $\omega_1$ exited from the optical parametric oscillator 103 is reflected by the mirror M2, and then is reflected by the dichroic mirror DM. The pulsed laser light of the optical frequency $\omega_2$ exited from the optical parametric oscillator 104 transmits through the dichroic mirror DM, and an optical path of the pulsed laser light of the optical frequency $\omega_2$ and an optical path of the pulsed laser light of the optical frequency $\omega_1$ are combined.

The pulsed laser lights of the optical frequencies $\omega_1$ and $\omega_2$ having the mutually combined optical path are incident on an incident end of the optical fiber 11 via the lens 105, and propagate in the optical fiber 11 to generate a point light source at an output end of the optical fiber 11. The pulsed laser lights of the optical frequencies $\omega_1$ and $\omega_2$ exited from the point light source are converted into a collimated light flux having a large diameter by the collector lens 12 to be incident on the diffraction grating 13, and then branched into diffracted light fluxes of respective orders. The diffracted light fluxes of respective orders are incident on the collecting lens 16, and then subjected to a collecting function of the collecting lens 16 to be collected at respective positions on a pupil conjugate plane 6A'.

Out of the diffracted light fluxes of respective orders, higher-order diffracted light fluxes of second-order and higher and a 0th-order diffracted light flux are blocked by the 0th-order light blocking mask 18 disposed in the vicinity of the pupil conjugate plane 6A', and ±first-order diffracted light fluxes pass through the 0th-order light blocking mask 18.

The ±first-order diffracted light fluxes passed through the 0th-order light blocking mask 18 form, by the lens 25, a plane conjugated with the diffraction grating 13 in the vicinity of the field stop 26 and then are converted into convergent lights by the field lens 27 to be reflected by the dichroic mirror 7, and then are collected at mutually different positions on a pupil plane 6A of the objective lens 6. Note that the collecting position of the + first-order diffracted light flux and the collecting position of the − first-order diffracted light flux are symmetrical with respect to an optical axis AZ of the objective lens 6.

The respective ± first-order diffracted light fluxes collected on the pupil plane 6A are turned into collimated light fluxes to exit from the tip of the objective lens 6, and then interfere with each other on a surface of the sample 5 to form interference fringes having a cyclic illumination distribution, specifically interference fringes having a sinusoidal illumination distribution. By the interference fringes (structured illumination), the sample 5 is spatially modulated.

The sample 5 is a fluorescent sample such as a fluorescent-stained organism. When the sample 5 is spatially modulated by the interference fringes, a moiré fringe corresponding to a difference between a pitch structure of the interference fringes and a pitch structure of a fluorescent area exhibiting in the sample 5 appears. On the moiré fringe, a structure of high frequency in the fluorescent area is shifted to a side of frequency that is lower than the original frequency, so that the fluorescence that exhibits this structure is directed to the objective lens 6 at an angle smaller than the original angle. Therefore, when the sample 5 is spatially modulated, even structural information of high frequency of the fluorescent area is transmitted by the objective lens 6.

The fluorescence generated in the spatially modulated sample 5 is incident on the objective lens 6, and converted into a collimated light flux by the objective lens 6, and after that, the collimated light flux transmits through the dichroic mirror 7 to perform a modulating image formation of the fluorescent area on an imaging plane of the imaging sensor 35 via the second objective lens 32.

The modulating image formation performed on the imaging plane of the imaging sensor 35 is converted into a modulated image, which is an electrical signal, by the imaging sensor 35. The image storage-calculation device 40 performs a demodulating calculation on this modulated image, to thereby generate a demodulated image. This demodulated image corresponds to a super-resolution image of the fluorescent area. This super-resolution image is stored in an internal memory (not illustrated) of the image storage-calculation device 40, and at the same time, is sent to a not-illustrated image display device.

Here, also in the ST-SIM, a plurality of modulated images different in phase of interference fringes are required for the purpose of performing a demodulating calculation, similarly to the 2D-SIM. It is assumed here that the mechanism 13A shifts the diffraction grating 13 in a direction of the pitch structure in order to shift a phase of an interference fringe. Note that here, a necessary number of modulated images different in phase of interference fringes (phase number) varies depending on an intensity of stimulation light (to be described later), but becomes at least "5 or more" in the St-SIM. Thus, an explanation is performed with the necessary phase number set to "5" here. Note that a timing at which a phase of an interference fringe is shifted by the mechanism 13A is controlled by the controlling device 39.

Further, also in the ST-SIM, a plurality of modulated images different in direction of interference fringes are required for the purpose of obtaining a super-resolution effect over plural directions of the sample 5, similarly to the 2D-SIM. It is assumed here that the mechanism 13A rotates the diffraction grating 13 around the optical axis AZ in order to change over a direction of an interference fringe. In the ST-SIM, a necessary number of modulated images different in direction of interference fringes (direction number) is determined as necessary. Incidentally, when the direction number is 4, a rotation position of the diffraction grating 13 is switched among four positions different by 45°. Note that a timing at which a direction of an interference fringe is changed over by the mechanism 13A is controlled by the controlling device 39.

Next, the pulsed laser light of the optical frequency $\omega_1$ and the pulsed laser light of the optical frequency $\omega_2$ are explained.

As described above, in the ST-SIM, the pulsed laser light of the optical frequency $\omega_1$ and the pulsed laser light of the optical frequency $\omega_2$ are used as a pulsed laser light that spatially modulates the sample 5.

Between the pulsed laser light of the optical frequency $\omega_1$ and the pulsed laser light of the optical frequency $\omega_2$, a diffraction angle at the diffraction grating 13 differs, so that collecting positions at the pupil plane 6A are slightly displaced.

However, between the pulsed laser light of the optical frequency $\omega_1$ and the pulsed laser light of the optical frequency $\omega_2$, an illumination distribution (distribution shape and spatial frequency) of interference fringes formed on the sample 5 is common. This is because the diffraction grating 13 and the sample 5 are conjugated with each other and an imaging magnification does not depend on an optical frequency (wavelength). Therefore, a spatial frequency of an interference fringe of the optical frequency $\omega_1$ and a spatial frequency of an interference fringe of the optical frequency $\omega_2$ are set to "K."

Further, in the ST-SIM of this embodiment, a difference between an optical path length of the pulsed laser light of the optical frequency $\omega_1$ and an optical path length of the pulsed laser light of the optical frequency $\omega_2$ is set to zero beforehand.

Therefore, in the ST-SIM of this embodiment, a timing at which the pulsed laser light of the optical frequency $\omega_1$ illuminates the sample 5 and a timing at which the pulsed laser light of the optical frequency $\omega_2$ illuminates the sample 5 coincide.

First, when the pulsed laser light of the optical frequency $\omega_1$ illuminates the sample 5, an energy level of some electrons of a fluorescent substance existing in the sample 5 shifts to an excitation level (excitation). That is, the pulsed laser light of the optical frequency $\omega_1$ has a function to excite electrons.

However, when the pulsed laser light of the optical frequency $\omega_2$ illuminates the sample 5 simultaneously with the pulsed laser light of the optical frequency $\omega_1$, an energy level of the excited electrons shifts to a base level (stimulated emission) and a stimulated emission light of the optical frequency $\omega_2$ is generated. That is, the pulsed laser light of the optical frequency $\omega_2$ has a function to stimulated emit excited electrons.

Therefore, the pulsed laser light of the optical frequency $\omega_1$ that illuminates the sample 5 will be referred to as an "excitation light" and the pulsed laser light of the optical frequency $\omega_2$ that illuminates the sample 5 will be referred to as a "stimulation light" below. Note that the optical frequency $\omega_1$ of the excitation light and the optical frequency $\omega_2$ of the stimulation light are each desirably set to fall within a range of from ultraviolet region to near-infrared region wavelengths in terms of a wavelength. These wavelengths are desirably selected according to a fluorescent dye used for the sample 5.

Further, the excitation light and the stimulation light both illuminate the sample 5, and nevertheless, spontaneous emission further occurs in the electros at an excitation level, and a spontaneously emitted light of an optical frequency $\omega_f$ lower than the optical frequency $\omega_1$ (fluorescence) is generated. Further, most of the excitation light illuminated the sample 5 passes thought the sample 5, and most of the stimulation light illuminated the sample 5 passes through the sample 5.

Figure 2A:
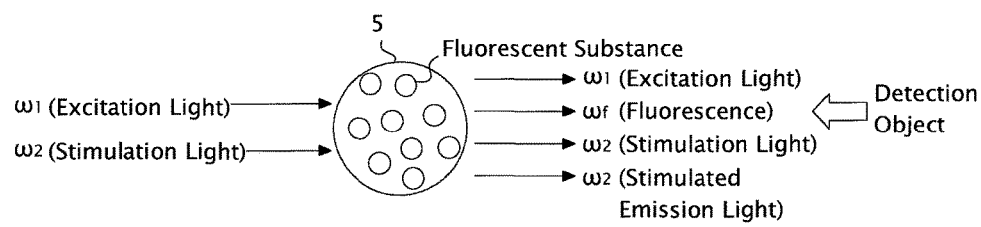
FIGS. 2A and 2B are diagrams explaining lights that are incident on a sample 5 and lights exited from the sample 5 in the ST-SIM.

Thus, as illustrated in FIG. 2A, lights to exit from the sample 5 in accordance with the excitation light and the stimulation light in the ST-SIM are four types below.

(1) The excitation light of the optical frequency $\omega_1$
(2) The stimulation light of the optical frequency $\omega_2$
(3) The stimulated emission light of the optical frequency $\omega_2$
(4) The fluorescence of the optical frequency $\omega_f$ In the ST-SIM, only the fluorescence of the optical frequency $\omega_f$ out of the above is set to a detection object.

Figure 2B:
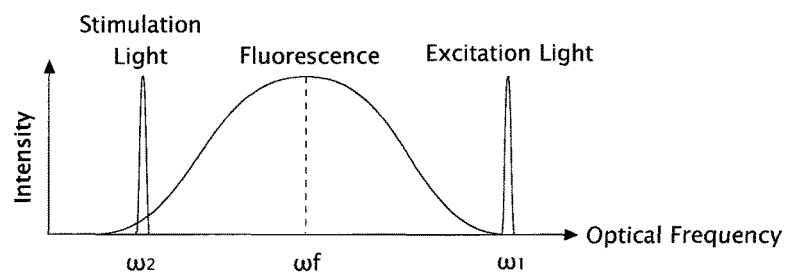

However, as illustrated in FIG. 2B, a range of the optical frequency of the fluorescence is broad, resulting in that the optical frequency $\omega_2$ of the stimulation light partially overlaps with the optical frequency of the fluorescence.

Thus, in the ST-SIM of this embodiment, in order to detect only the fluorescence having a broad optical frequency range with a high degree of accuracy, the controlling device 39 employs such a configuration as to synchronously control the laser unit 100 and the imaging sensor 35, to thereby make a timing of the imaging sensor 35 imaging a modulated image (timing of charge storing of the imaging sensor 35) deviate from a timing of the stimulation light illuminating the sample 5. However, a pulse width of the excitation light and a pulse width of the stimulation light are each desired to be shorter than a fluorescence lifetime.

Accordingly, in the ST-SIM of this embodiment, it is possible to prevent noise components due to the stimulation light and the stimulated emission light from being superimposed on the modulated image.

Incidentally, in the ST-SIM of this embodiment, the timing of the excitation light illuminating the sample 5 coincides with the timing of the stimulation light illuminating the sample 5, resulting in that the timing of the imaging sensor 35 imaging a modulated image automatically deviates from the timing of the excitation light illuminating the sample 5.

Accordingly, in the ST-SIM of this embodiment, it is possible to prevent a noise component due to the excitation light from being superimposed on the modulated image.

Figure 3:
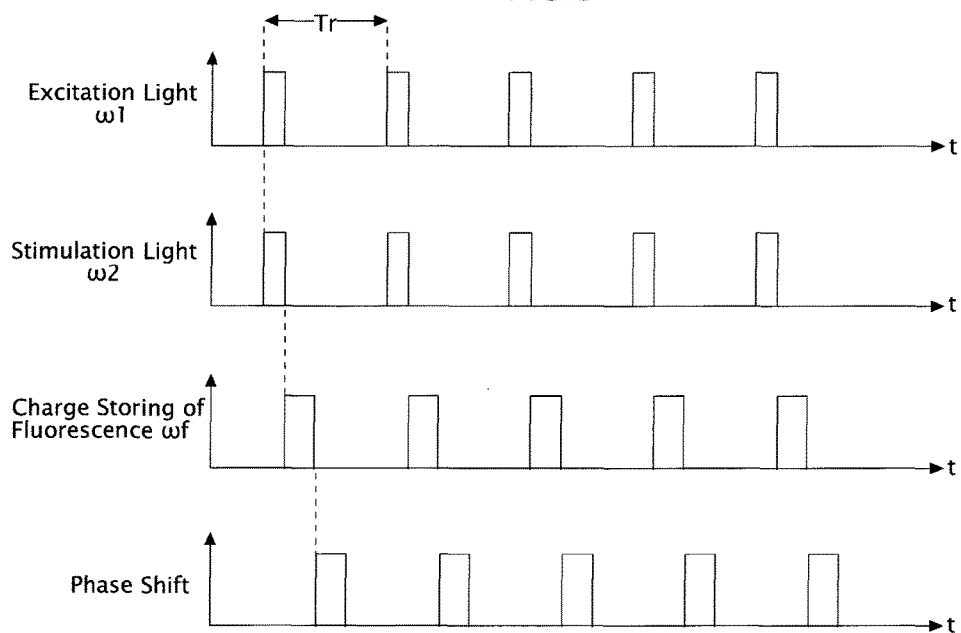
FIG. 3 is a timing chart of the ST-SIM of the first embodiment.

FIG. 3 is a timing charts illustrating a relation among the timing of the excitation light illuminating the sample 5, the timing of the stimulation light illuminating the sample 5, the timing of charge storing of the imaging sensor 35, and a phase shifting timing of an interference fringe.

The controlling device 39 of this embodiment, as illustrated in the first and second rows of FIG. 3, makes the excitation light and the stimulation light illuminate the sample 5 simultaneously, and at the same time, repeats this illumination at a pitch Tr=1/fr. This pitch Tr is desired to be longer than a fluorescence lifetime of the fluorescent substance that has stained the sample 5. Therefore, fluorescence light emission and attenuation from the sample 5 are repeated at the pitch Tr.

Further, the controlling device 39 of this embodiment, as illustrated in the third row of FIG. 3, performs charge storing of the imaging sensor 35 at a timing at which illuminations of the excitation light and the stimulation light are finished and fluorescence light emission is being performed within one pitch Tr. At this timing, the excitation light, the stimulation light, and the stimulated emission light are not incident on the imaging sensor 35, and only the fluorescence is incident on the imaging sensor 35. Therefore, on a modulated image generated by the charge storing, a noise component due to the excitation light, a noise component due to the stimulation light, and a noise component due to the stimulated emission light are all not superimposed.

Further, the controlling device 39 of this embodiment, as illustrated in the fourth row of FIG. 3, performs phase shifting of an interference fringe at a timing at which charge storing of the imaging sensor 35 is finished within one pitch Tr.

Further, the controlling device 39 of this embodiment repeats the above processes, which are set as one round, only for five rounds (rounds $A_1$, $A_2$, $A_3$, $A_4$, and $A_5$), and acquires modulated images for five phases.

Further, the controlling device 39 of this embodiment repeats the acquisitions of modulated images for five phases (rounds $A_1$, $A_2$, $A_3$, $A_4$, and $A_5$) while changing over a direction of an interference fringe, and acquires, for example, 20 modulated images, which are equal to modulated images of five phases× four directions.

Note that the controlling device 39 of this embodiment sets the repetition pitch Tr of a series of processes made of illuminations of the excitation light and the stimulation light, charge storing of the imaging sensor 35, and phase shifting of an interference fringe to be longer than the fluorescence lifetime, and thus it is also possible to prevent crosstalk between two modulated images consecutive in terms of time. The "crosstalk" mentioned here means a phenomenon in which fluorescence that should be reflected in a modulated image of the preceding frame is reflected in a modulated image of the subsequent frame.

Figure 4A:
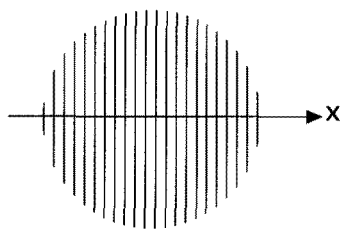
FIGS. 4A to 4D are diagrams explaining a relation among an interference fringe by means of an excitation light, an interference fringe by means of a stimulation light, and a synthesized interference fringe.

Next, the interference fringes in the ST-SIM are explained in detail. FIGS. 4A to 4D are diagrams explaining the interference fringes in the ST-SIM, and a symbol "x" in each of FIGS. 4A to 4D denotes, as illustrated in FIG. 4A, a direction in which the sample 5 is modulated by means of the interference fringes.

Figure 4B:
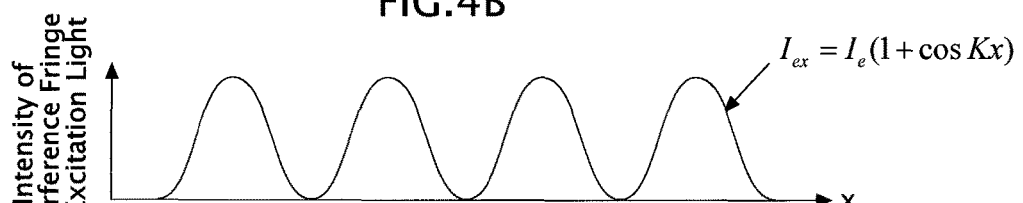

First, an interference fringe $I_{ex}(x)$ by means of the excitation light as a single light is, as illustrated in FIG. 4B, expressed by $I_{ex}(x)=I_e(1+\cos Kx)$. This interference fringe $I_{ex}(x)$ has a sinusoidal intensity distribution, and is made of a component of spatial frequency zero and a component of spatial frequency K.

Figure 4C:
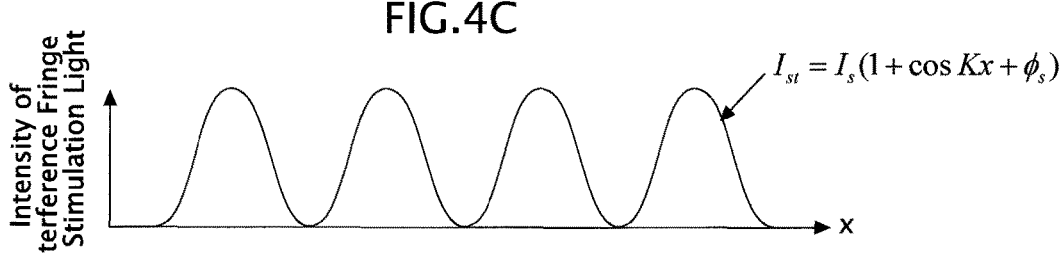
Figure 4D:
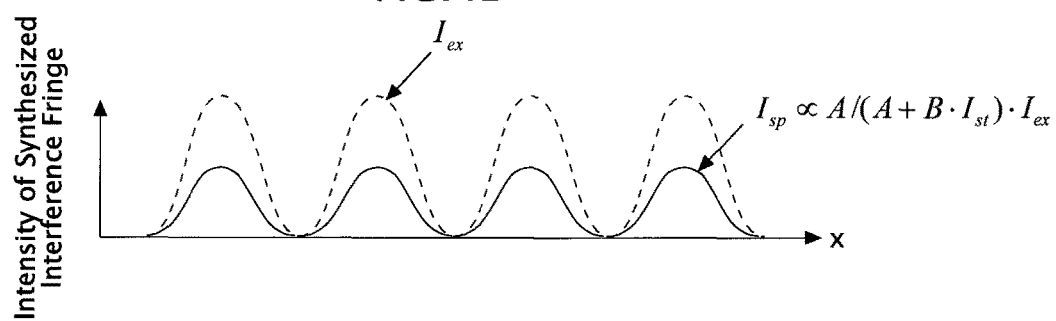

Next, an interference fringe $I_{st}(x)$ by means of the stimulation light as a single light is, as illustrated in FIG. 4C, expressed by $I_{st}(x)=I_s(1+\cos Kx+\phi_s)$. This interference fringe $I_{st}(x)$ also has a sinusoidal intensity distribution, and is made of a component of spatial frequency zero and a component of spatial frequency K. Here, $\phi_s$ means a phase difference of the stimulation light with respect to the excitation light. Note that in FIG. 4C, the case of $\phi_s=0$ is illustrated.

Then, the sample 5 in the ST-SIM can be regarded as being illuminated by a synthesized interference fringe $I_{sp}(x)$ in which two types of the above interference fringes $I_{ex}(x)$ and $I_{st}(x)$ are formed mutually as illustrated in FIG. 4C. This synthesized interference fringe $I_{sp}(x)$ is expressed by a mathematical expression (1) below.

$$I_{sp} \propto A/(A+B \cdot I_{st}(x)) \cdot I_{st}(x) \qquad (1)$$

Note that in the expression (1), "A" denotes a coefficient contributing to fluorescence, and "B" denotes a coefficient contributing to stimulated emission. Further, the expression (1) is an approximate expression.

This synthesized interference fringe $I_{sp}(x)$ has a high-frequency component, which is slightly different from the sinusoidal intensity distribution. Specifically, in the synthesized interference fringe $I_{sp}(x)$, a component of spatial frequency zero, a component of spatial frequency K, and a frequency component of spatial frequency mK are contained (where m is a modulation order of 2 or more and m=2, 3, 4, . . . is satisfied).

Figure 5A:
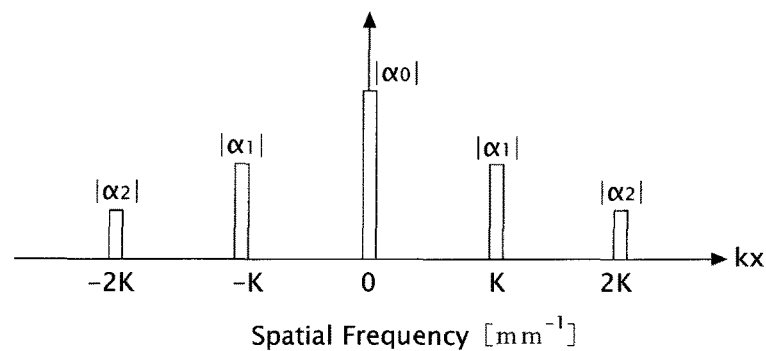
FIGS. 5A and 5B are diagrams explaining a Fourier spectrum of the synthesized interference fringe and various modulated components contained in a modulated image.
Figure 5B:
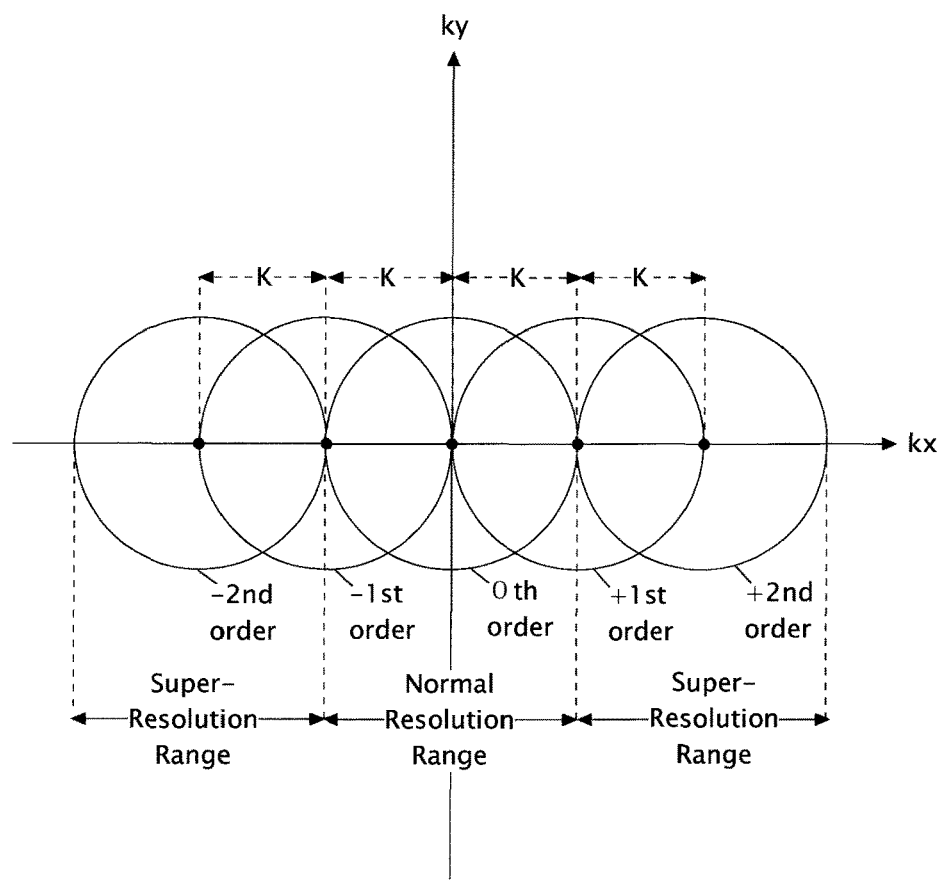

As above, the ST-SIM having an illumination pattern (the synthesized interference fringe $I_{sp}(x)$) that modulates the sample 5, in which the component of spatial frequency zero, the component of spatial frequency K, and the component of spatial frequency 2K or more are contained, can expand a super-resolution range as compared to a 2D-SIM having an illumination pattern (two-beam interference fringes) that modulates the sample 5, in which only the component of spatial frequency zero and the component of spatial frequency K are contained (FIGS. 5A and 5B).

Further, in the ST-SIM, an upper limit value of the super-resolution range is determined by a maximum value of the modulation order m, and a value of the modulation order m depends on the intensity of stimulation light. Therefore, the larger the intensity of stimulation light is, the larger the maximum value of the modulation order m becomes, resulting in expansion of the super-resolution range (improvement in resolving power). However, as the maximum value of the modulation order m is larger, the necessary number of modulated images different in phase of interference fringes (phase number) increases, and thus a frame rate of the super-resolution image tends to decrease. This tendency is seen also in a NSIM similarly, and the expansion of super-resolution range (improvement in resolving power) and an improvement in frame rate are in a tradeoff relationship.

However, it is possible to make an amplitude $|\alpha_m|$ of the component of spatial frequency mK in the ST-SIM become larger than an amplitude of the component of spatial frequency mK in the NSIM, and therefore as long as the maximum value of the modulation order m is common between the ST-SIM and the NSIM, an OTF of the ST-SIM becomes higher in contrast than an OTF of the NSIM. Accordingly, the resolving power of the ST-SIM becomes higher than a resolving power of the NSIM.

Further, in the ST-SIM, the phase $\phi_s$ of the stimulation light based on the phase of the excitation light is set to $\phi_s=\pi[\text{rad}]$, thereby making it possible to also increase an amplitude $|\alpha_1|$ of the component of spatial frequency K while increasing the amplitude $|\alpha_m|$ of the component of spatial frequency 2K or more. Such a merit cannot be obtained in the NSIM. That is, in the NSIM, when the amplitude $|\alpha_m|$ of the component of spatial frequency 2K or more is increased, the amplitude of the component of spatial frequency K decreases, so that in terms of a certain spatial frequency, contrast decreases, which causes a decrease in resolving power.

Here, in order to set the phase $\phi_s$ of the stimulation light based on the phase of the excitation light to $\pi[\text{rad}]$, it is only necessary to utilize that the stimulation light and the excitation light having different wavelengths are spatially separated in the vicinity of the pupil plane 6A or pupil conjugate plane 6A' in FIG. 1.

For example, it is only necessary to insert a glass block only in an optical path of a + first-order diffracted light or − first-order diffracted light of the stimulation light at a surface in the vicinity of the pupil plane 6A or pupil conjugate plane 6A' and set a phase retardation amount due to the glass block to $(2n+1)\pi$. Here, n is an integer.

Alternatively, it is only necessary to dispose a spatial light modulator in the vicinity of the pupil plane 6A or pupil conjugate plane 6A' and set a phase retardation amount of an incident area of a + first-order diffracted light or − first-order diffracted light of the stimulation light to $(2n+1)\pi$ and set a phase retardation amount of the other area to zero in the spatial light modulator. Here, n is an integer.

Note that since the phase $\phi_s$ is the phase of the stimulation light based on the phase of the excitation light, in place of phase retarding the stimulation light, the excitation light may be phase retarded, or the stimulation light and the excitation light both may be phase retarded. However, when the stimulation light and the excitation light both are phase retarded, an appropriate difference is provided between both phase retardation amounts.

Alternatively, it is also possible that as the diffraction grating 13, a diffraction grating for excitation light and a diffraction grating for stimulation light are prepared and positions of the two diffraction gratings in a direction perpendicular to a grid line are displaced beforehand, to thereby set the phase $\phi_s$ of the stimulation light based on the phase of the excitation light to $\pi[\text{rad}]$.

Further, in order to reduce an artifact (error) caused by image processing, when an order to be used is set to m, an amplitude of an order (m+1) higher than the order m is desirably suppressed to be as small as possible. Further, when an amplitude $|\alpha_2|$ is made common between the ST-SIM and the NSIM, an amplitude $|\alpha_3|$ becomes smaller in the ST-SIM. Therefore, the ST-SIM can be said to be excellent also in terms of an artifact reduction.

That is, in the ST-SIM, by appropriately controlling the intensity and the phase of the stimulation light, a high-frequency component of spatial frequency 3K or more out of the frequency components contained in the illumination pattern (synthesized interference fringe $I_{sp}(x)$) can be reduced down to a negligible level (noise level).

Besides, the performance for super resolution in the ST-SIM is just merely performing the stimulation light illumination (stimulated emission by means of the stimulation light) in addition to the excitation light illumination (spontaneous emission by means of the excitation light) similar to that of the 2D-SIM, so that there is also no need to cause saturation by significantly increasing an intensity of the excitation light illumination like the NSIM. Therefore, it is possible to reduce damage of the sample 5 containing a biological sample or the like.

Hereinafter, an argument will be developed by assuming that the high-frequency component (of spatial frequency 3 k or more) contained in the synthesized interference fringe $I_{sp}(x)$ is negligible.

A Fourier spectrum of the synthesized interference fringe $I_{sp}(x)$ of the ST-SIM is as illustrated in FIG. 5A. Out of this Fourier spectrum, magnitude of a 0th-order Fourier spectrum (=an amplitude of the component of spatial frequency zero) is $|\alpha_0|$, magnitude of ±first-order Fourier spectra (=an amplitude of the component of spatial frequency K) is $|\alpha_1|$, magnitude of ±second-order Fourier spectra (=an amplitude of the component of spatial frequency 2K) is $|\alpha_2|$, and magnitude of a higher-order Fourier spectrum of third-order or higher (=an amplitude of the component of spatial frequency 3K or more) is zero (a noise level).

Then, when the sample 5 is spatially modulated by the synthesized interference fringe $I_{sp}(x)$ having this Fourier spectrum, as illustrated in FIG. 5B, on the modulated image, five modulated components of a 0th-order modulated component, a + first-order modulated component, a − first-order modulated component, a + second-order modulated component, and a − second-order modulated component are superimposed, and higher-order modulated components of third-order and higher are not superimposed. The reason why the phase number in this embodiment is set to 5 is to separate these five modulated components by performing a demodulating calculation.

Note that the 0th-order modulated component is information of a spatial frequency range where resolution is enabled by uniform illumination (=normal resolution range), the + first-order modulated component is information of a spatial frequency range deviating from the normal resolution range by +K, the + second-order modulated component is information of a spatial frequency range deviating from the normal resolution range by +2K, the − first-order modulated component is information of a spatial frequency range deviating from the normal resolution range by −K, and the − second-order modulated component is information of a spatial frequency range deviating from the normal resolution range by −2K.

That is, of the ST-SIM, the spatial frequency range where resolution is enabled by the synthesized interference fringe $I_{sp}(x)$ is 1.5 times a spatial frequency range where resolution is enabled by interference fringes of the 2D-SIM at the maximum (=twice the normal resolution range at the maximum), and is three times the normal resolution range at the maximum.

Next, with reference to FIG. 6, the demodulating calculation performed by the image storage-calculation device 40 is explained.

Here, for simplification, it is assumed that of the synthesized interference fringe, a phase number $N_{max}$ is 5 and a direction number $M_{max}$ is 1. In FIG. 6, symbols $I_r(1,1)$, $I_r(2,1)$, and $I_r(5,1)$ denote modulated images mutually different in phase of synthesized interference fringes, "N" in a modulated image $I_r(N,M)$ denotes a phase number of the synthesized interference fringe contributing to the modulated image, (which is 1 to 5, here), and "M" in the modulated image $I_r(N,M)$ denotes a direction number of the synthesized interference fringe contributing to the modulated image, (which is 1, here).

The demodulating calculation performed by the image storage-calculation device 40 includes steps (A) to (E) below.

(A) The image storage-calculation device 40, as illustrated in the part (a) of FIG. 6, individually Fourier transforms $N_{max} \times M_{max}$ frames (five frames, here) of modulated images.

(B) The image storage-calculation device 40, as illustrated in the part (b) of FIG. 6, performs separation of modulated components among $N_{max}$ frames (five frames, here) of modulated images with common directions of synthesized interference fringes.

(C) The image storage-calculation device 40, as illustrated in the part (c) of FIG. 6, rearranges each of the mutually separated five modulated components.

(D) The image storage-calculation device 40, as illustrated in the part (d) of FIG. 6, weight-synthesizes the rearranged five modulated components on the same wave number space, to thereby generate a demodulated image $O_k$ whose spatial frequency range is expanded.

(E) The image storage-calculation device 40, as illustrated in the part (e) of FIG. 6, inverse Fourier transforms the demodulated image $O_k$, to thereby generate a super-resolution image $O_r$ of the samples.

Next, principles of the steps (B) to (E) are explained.

First, a sample coordinate in a modulating direction is set to x, a point image intensity distribution of an imaging optical system (the objective lens 6, the second objective lens 32) is set to $P_r(x)$, a structure of a fluorescence area in the sample 5 is set to $O_r(x)$, modulation orders I of the sample 5 by the synthesized interference fringe are set to −2, −1, 0, 1, and 2, a spatial frequency of first-order modulation of the sample 5 by the synthesized interference fringe is set to K, a phase of the synthesized interference fringe is set to ϕ, and an amplitude of the synthesized interference fringe is set to $m_l$, and then the modulated image is expressed by an expression (2) below.

$$I_r(x) = \sum_l m_l(O_r(x)\exp(ilKx + il\phi) * P_r(x)) \quad (2)$$

Note that a symbol "*" in the expression (2) denotes a convolution integral. Here, in order to distinguish an amount in a real space and an amount in the wave number space, a subscript "r" is added to the amount in the real space, and a subscript "k" is added to the amount in the wave number space.

Thereby, a resultant from the modulated image $I_r(x)$ being Fourier transformed ($=I_k(k)$) is expressed by an expression (3) below.

$$I_k(k) = \sum_l m_l\exp(il\phi)O_k(k + IK)P_k(k) \quad (3)$$

Note that a resultant from the point image intensity distribution $P_r(x)$ of the imaging optical system being Fourier transformed ($=P_k(k)$) corresponds to an optical transfer function (OTF: Optical Transfer Function) of the imaging optical system.

Here, $O_k(k+IK)$ (I=−2, −1, 0, 1, and +2) in the expression (3) means modulated components of respective orders superimposed on a modulated image $I_k(k)$. With regard to the first-order modulated component $O_k(k+K)$ and the − first-order modulated component (k−K), each actual spatial frequency component of the sample 5 is shifted (to a side of low frequency) by K. Further, with regard to the second-order modulated component $O_k(k+2K)$ and the − second-order modulated component (k−2K), each actual spatial frequency component of the sample 5 is shifted (to a side of low frequency) by 2K. The larger this shift amount is, the larger a super-resolution effect becomes. Therefore, the value of spatial frequency "K" of the first-order modulation by the synthesized interference fringe is desirably set to a value as high as possible within a range where the imaging optical system can form an image.

Then, out of $N_{max} \times M_{max}$ frames (five frames, here) of the modulated images, $N_{max}$ frames (five frames, here) of the modulated images, which have common directions and different phases of the synthesized interference fringes, are different only in ϕ and common in $m_l$ and K. Therefore, when a phase of a synthesized interference fringe reflected in a modulated image of a jth frame out of these $N_{max}$ frames (five frames, here) is set to $\phi_j$, a modulated image $I_{kj}(k)$ of the jth frame is expressed by an expression (4) below.

$$I_{kj}(k) = \sum_l m_l\exp(il\phi_j)O_k(k + IK)P_k(k) \quad (4)$$

Therefore, in the step (B), five equations obtained by $N_{max}$ frames (five frames, here) of the modulated images $I_{kj}(k)$ are solved simultaneously, thereby enabling the modulated components $O_k(k+IK)$ of respective orders (I=−2, −1, 0, 1, and +2) each to be known (separated from one another). Incidentally, $P_k(k)$ in this expression (4) is peculiar to the imaging optical system, and thus can be measured beforehand.

Note that when the modulated components $O_k(k+IK)$ of respective orders (I=−2, −1, 0, 1, and +2) are separated from one another, $O_k(k+IK)P_k(k)$ (I=−2, −1, 0, 1, and +2) each may be made known, and then these may be divided by a value of $P_k(k)$, but in place of performing a simple division, a well-known means that is hardly affected by noise, which is a Wiener filter or the like, may also be utilized.

Then, in the step (C), it is only necessary to shift (rearrange) the ±first-order modulated components $O_k(k+K)$ and $O_k(k-K)$ over a kx direction by a modulation frequency K and at the same time, shift (rearrange) the ±second-order modulated components $O_k(k+2K)$ and $O_k(k-2K)$ over a kx direction by a modulation frequency 2K.

Further, in the step (D), it is only necessary to weight-synthesize the modulated components $O_k(k+IK)$ of respective orders (I=−2, −1, 0, 1, and +2) on the wave number space, thereby generating a demodulated image $O_k(kx)$ having a broad frequency range.

Therefore, in the step (E), this demodulated image $O_k(kx)$ is inverse Fourier transformed, thereby obtaining a super-resolution image $O_r(x)$ of the sample 5. This super-resolution image $O_r(x)$ has a super-resolution over the modulating direction of the synthesized interference fringe (x direction).

Incidentally, since the phase number $N_{max}$ is assumed to be 5 here, the modulated component separation is performed by solving simultaneous equations, but when the phase number $N_{max}$ is greater than 5, the separation may be performed by a method disclosed in WO 2006/109448.

Further, although the steps (C) and (D) are performed in order here, it is also possible to perform the steps (C) and (D) by using a collective arithmetic expression. As the arithmetic expression, a mathematical expression (1) in Online Methods disclosed in "Super-Resolution Video Microscopy of Live Cells by Structured Illumination", Peter Kner, Bryant B. Chhun, Eric R. Griffis, Lukman Winoto, and Mats G. L. Gustafsson, NATURE METHODS Vol. 6 NO. 5, pp. 339-342, (2009) or the like is applicable.

Further, although the demodulating calculation when the direction number $M_{max}=1$ is set is explained here, it goes without saying that the direction number $M_{max}$ may be set to 2 or more.

Figure 7:
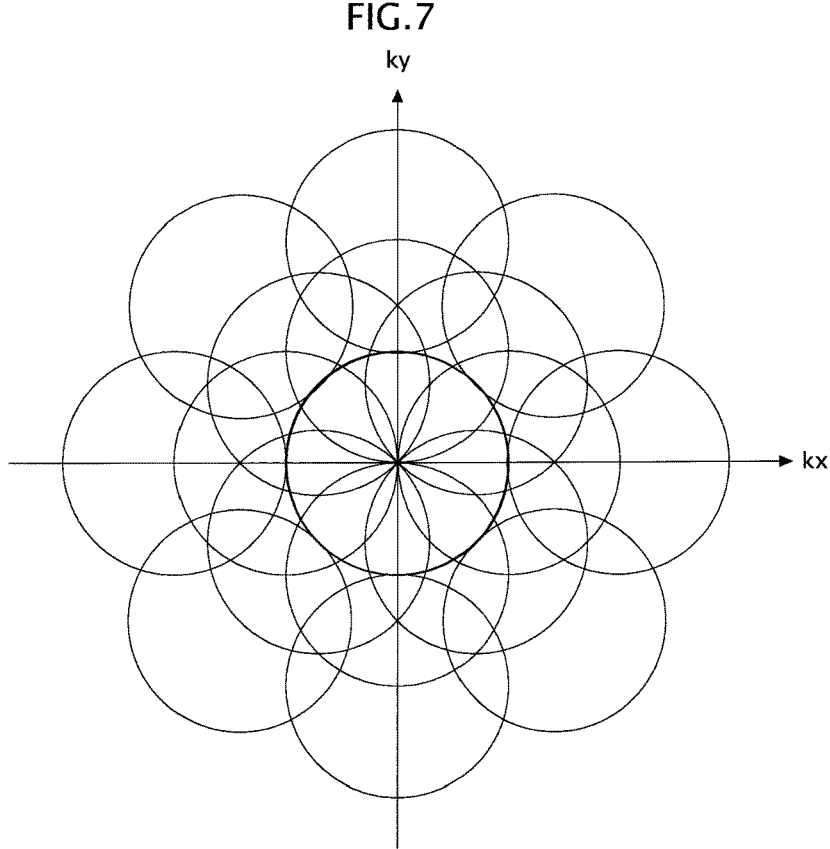
FIG. 7 is an example of a resolution range when a direction number $M_{max}=4$ is set.

For example, when modulated images of five phases are acquired by using each of synthesized interference fringes in four directions different by 45° (20 modulated images in total are acquired) and the steps (B) to (D) are performed for each of the directions of synthesized interference fringes, as illustrated in FIG. 7, a resolution range can be expanded over the respective four directions.

Second Embodiment

Hereinafter, as a second embodiment of the present invention, a modified example of the first embodiment (ST-SIM) will be explained. Only differences from the first embodiment are explained here.

A controlling device 39 of this embodiment acquires a modulated image $I_A$ being a fluorescence image of a sample 5 in a state where both of an excitation light and a stimulation light are incident, and at the same time, acquires a modulated image $I_B$ being a fluorescence image of the sample 5 in a state where only the former of the excitation light and the stimulation light is incident, to then send the modulated images $I_A$ and $I_B$, which are set as one set, to an image storage-calculation device 40.

An interference fringe contributing to the modulated image $I_A$ is the synthesized interference fringe explained in the first embodiment, and an interference fringe contributing to the modulated image $I_B$ is the interference fringe by means of the excitation light as a single light. Further, phases and directions of the interference fringes are common between the modulated images $I_A$ and $I_B$ making a set mutually.

The image storage-calculation device 40 of this embodiment generates a difference image $I_D = I_B - I_A$ between the modulated image $I_B$ and the modulated image $I_A$ making a set mutually, and performs a demodulating calculation similar to that of the modulated images of the first embodiment on the difference image $I_D$, to thereby generate a super-resolution image.

Figure 8:
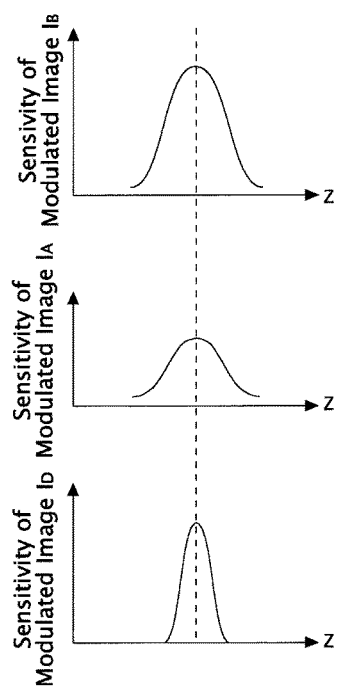
FIG. 8 is diagram explaining an intensity distribution of interference fringes by an excitation light in an optical axis direction, an intensity distribution of synthesized interference fringes in an optical axis direction, and an intensity distribution of difference interference fringes in an optical axis direction.

FIG. 8 is a diagram where sensitivity of the modulated image $I_B$, sensitivity of the modulated image $I_A$, and sensitivity of the difference image $I_D$ are compared. Note that "sensitivity of image" mentioned here means an intensity distribution of fluorescence than can be reflected from the sample 5 to an image, and corresponds to a luminance distribution of an image of the case where a fluorescent substance exists over an optical axis direction of the sample 5 with a uniform density.

The first row of FIG. 8 schematically illustrates a sensitivity distribution of the modulated image $I_B$ in an optical axis direction (z direction), the second row of FIG. 8 schematically illustrates a sensitivity distribution of the modulated image $I_A$ in an optical axis direction (z direction), and the third row of FIG. 8 schematically illustrates a sensitivity distribution of the difference image $I_D$ in an optical axis direction (z direction). In FIG. 8, dotted lines each indicate an observation object plane inside the sample 5, which corresponds to a focal plane of an objective lens 6.

First, as illustrated in the first row of FIG. 8, according to a sensitivity distribution curve of the modulated image $I_B$, even fluorescence from a plane deviating from the observation object plane affects the modulated image $I_B$, so that a background component (one type of noise) is superimposed on the modulated image $I_B$. Note that the sensitivity distribution curve of the modulated image $I_B$ contains the component of spatial frequency zero and the component of spatial frequency K over the previously described x direction, which is not illustrated in the first row of FIG. 8.

Next, as illustrated in the second row of FIG. 8, according to a sensitivity distribution curve of the modulated image $I_A$, even fluorescence from a plane deviating from the observation object plane affects the modulated image $I_A$, so that a background component (one type of noise) is superimposed on the modulated image $I_A$. However, the interference fringe contributing to the modulated image $I_A$ (=synthesized interference fringe) causes a large number of stimulated emission lights to be generated on the observation object plane, so that fluorescence to generate from the observation object plane decreases by an amount of the generated stimulated emission lights. Therefore, a peak of the sensitivity distribution curve in the second row of FIG. 8 is positioned lower than a peak of the sensitivity distribution curve in the first row of FIG. 8. This is ascribed to the fact that an intensity of stimulated emission light is proportional to a product of an intensity of excitation light and an intensity of stimulation light. Note that the sensitivity distribution curve of the modulated image $I_A$ contains not only the component of spatial frequency zero and the component of spatial frequency K but also the component of spatial frequency 2K or more over the previously described x direction, which is not illustrated in the second row of FIG. 8. This is as expressed by the expression (1).

Next, as illustrated in the third row of FIG. 8, according to a sensitivity distribution curve of the difference image $I_D$, fluorescence from a plane deviating from the observation object plane does not affect the difference image $I_D$. This difference image $I_D$ expresses a decrease $\Delta I_{FL}$ in fluorescence caused by the stimulated emission light. This decrease $\Delta I_{FL}$ is expressed by an expression (5). That is, this difference image $I_D$ indirectly expresses an image of the sample 5 generated by means of the stimulated emission light. Note that the sensitivity distribution curve of the difference image $I_D$ contains not only the component of spatial frequency zero and the component of spatial frequency K but also the component of spatial frequency 2K or more over the previously described×direction, which is not illustrated in the third row of FIG. 8.

$$\Delta I_{FL}(x) = B \cdot I_{st}(x) \cdot I_{ex}(x)/(A + B \cdot I_{st}(x)) \quad (5)$$

However, the expression (5) is an approximate expression.

As described above, in a ST-SIM of this embodiment, it is possible to remove an additional fluorescence that is generated in a plane other than the focal plane. This additional fluorescence reduces contrast of structured illumination, to thus become a problem, which is part of the reason for limiting performance of deep portion observation.

Accordingly, the ST-SIM of this embodiment that removes an effect of additional fluorescence can achieve not only the same effect as that of the ST-SIM of the first embodiment, but also a deep portion observation effect of the sample 5.

FIG. 9 is a timing chart of this embodiment. Here, only differences from the timing chart illustrated in FIG. 3 are explained.

As illustrated in FIG. 9, the controlling device 39 of this embodiment, similarly to the controlling device 39 of the first embodiment, also executes rounds $A_1$, $A_2$, $A_3$, $A_4$, and $A_5$ in order. By executing these rounds $A_1$, $A_2$, $A_3$, $A_4$, and $A_5$, five modulated images $I_A$ that are modulated by synthesized interference fringes, (where only phases are different), are acquired.

However, the controlling device 39 of this embodiment executes a round $B_i$ between a round $A_{(i-1)}$ and a round $A_i$. The round $B_i$ is to halt stimulation light illumination and phase shifting in the round $A_i$, and waveforms illustrated by dotted lines in the second and fourth rows of FIG. 9 each mean a halt. By executing such a round $B_i$(i=1 to 5), five modulated images $I_B$ that are modulated by interference fringes by means of an excitation light as a single light, (where only phases are different), are acquired.

Accordingly, the controlling device 39 of this embodiment can continuously acquire the modulated images $I_B$ and $I_A$ making a set mutually.

Note that in this embodiment, the controlling device 39 acquires two types of the modulated images $I_A$ and $I_B$ and at the same time, the image storage-calculation device 40 takes a difference between the modulated images $I_A$ and $I_B$, to thereby structure a modulated image (=the difference image $I_D$) to be an object of a demodulating calculation, but a method of structuring the difference image $I_D$ is not limited to this.

For example, the controlling device 39 of this embodiment may structure the difference image $I_D$ by modulating an intensity of the stimulation light at a frequency f1 over a time direction and at the same time, lock-in detecting a spontaneously emitted light (fluorescence) generated in the sample 5 at a detection frequency f1 by using a lock-in camera.

Alternatively, the controlling device 39 of this embodiment may structure the difference image $I_D$ by modulating an intensity of the excitation light at a frequency f1 over a time direction and at the same time, lock-in detecting a stimulated emission light generated in the sample 5 at a detection frequency f1 by using a lock-in camera.

Supplements of Embodiments

Incidentally, since in the ST-SIM of each of the above-described embodiments, out of the components of spatial frequencies contained in the synthesized interference fringe, the range of spatial frequency to be suppressed to a negligible level (noise level) is set to "3K or more," the necessary phase number $N_{max}$ results in "5."

However, in the ST-SIM of the first embodiment or second embodiment, the range of spatial frequency to be suppressed may be set to "4K or more," "5K or more," "6K or more," . . . , or the like.

For example, when the range of spatial frequency to be suppressed is "4K or more," the necessary phase number $N_{max}$ becomes "7," and when the range of spatial frequency to be suppressed is "5K or more," the necessary phase number $N_{max}$ becomes "9."

Further, although in the ST-SIM of the first embodiment, the phase shifting pitch is set to Tr, it is also possible to set the phase shifting pitch to n·Tr (where n is an integer of 2 or more) and average n pieces of modulated images with common directions and phases of interference fringes, to generate a modulated image having a high SN ratio.

Further, although in the ST-SIM of the second embodiment, the phase shifting pitch is set to 2Tr, it is also possible to set the phase shifting pitch to 2n·Tr (where n is an integer of 2 or more) and average each of n pieces of modulated images $I_A$ and n pieces of modulated images $I_B$ with common directions and phases of interference fringes, to generate modulated images $I_A$ and $I_B$ having a high SN ratio.

Further, although in the ST-SIM of each of the above-described embodiments, the timing of the excitation light and the stimulation light illuminating the sample 5 is made to deviate from the timing of charge storing of the imaging sensor 35 for the purpose of making the fluorescence exited from the sample 5 become a detection object, the both timings may be made to coincide with each other.

However, in this case, it is only necessary to dispose a wavelength selection filter between the sample 5 and the imaging sensor 35, to provide a wavelength selecting property in which the wavelength selection filter blocks a light of the optical frequency ($\omega_1$) that is the same as that of the excitation light and blocks a light of the optical frequency ($\omega_2$) that is the same as that of the stimulation light and the stimulated emission light, and allows a light of the optical frequency ($\omega_f$) that is the same as that of the fluorescence to pass therethrough.

Further, although in the ST-SIM of each of the above-described embodiments, the timing at which the excitation light illuminates the sample 5 and the timing at which the stimulation light illuminates the sample 5 are made to coincide with each other, the stimulation light may illuminate the sample 5 after illumination of the excitation light. However, an illumination timing deviation between the excitation light and the stimulation light is desired to be sufficiently small as compared to the fluorescence lifetime.

Further, although in the ST-SIM of each of the above-described embodiments, the charge storing of the imaging sensor 35 is started immediately after the stimulation light illuminates the sample 5, a timing at which the charge storing is started may be delayed by $\Delta T$. By a delay by $\Delta T$, an effect similar to that of increasing the illumination intensity of stimulation light can be obtained. This is because as the illumination intensity of stimulation light is stronger in a place of the sample 5, the fluorescence lifetime in the place becomes shorter, and fluorescence generated in the place with a short fluorescence lifetime is exempted from the detection object of the imaging sensor 35 due the delay by $\Delta T$, resulting in that fluorescence quenching efficiency improves. Therefore, when it is imagined that the quenching efficiency is set to be equal, the illumination intensity of stimulation light can be made smaller when $\Delta T$ is introduced than when it is not introduced. However, $\Delta T$ is desired to be shorter than the fluorescence lifetime.

Further, although in the ST-SIM of each of the above-described embodiments, both the excitation light and the stimulation light are regarded as a pulsed light, at least one of the excitation light and the stimulation light may be set to a CW light.

Further, when both the excitation light and the stimulation light are set to a CW light in the ST-SIM of each of the above-described embodiments, it is possible to arbitrarily set the imaging timing and the phase shifting timing.

However, when the CW light (CW laser) is utilized, a filter is desirably introduced in order to detect only the fluorescence.

Further, although the ST-SIM of each of the above-described embodiments is one in which the present invention is applied to a transmission microscope, the present invention is applicable also to a reflection microscope.

Further, the demodulating calculation executed in the ST-SIM of each of the above-described embodiments may be executed by a hardware, or may also be executed by a software.

Further, although the 2D-SIM having the present invention applied thereto has been explained in the above-described both embodiments, the present invention is applicable also to a 3D-SIM. This makes it possible to achieve the resolution improving effect also over the optical axis direction.

Incidentally, the 3D-SIM is that not two-beam interference fringes but three-beam interference fringes are used as the interference fringe used for spatially modulating the sample 5. Therefore, in the 3D-SIM, it is only necessary to use, for example, a higher-order light blocking mask in place of the 0th-order light blocking mask 18 and introduce not only the + first-order diffracted light and the − first-order diffracted light but also a 0th-order diffracted light into the sample 5. However, in the 3D-SIM having the present invention applied thereto, the necessary number of modulated images different in phase of interference fringes (phase number) is increased as compared to the 2D-SIM having the present invention applied thereto. Incidentally, the phase number necessary for expanding an OTF of the 3D-SIM having the present invention applied thereto equally to the OTF of the case where up to the 2K component is utilized in the 2D-SIM having the present invention applied thereto becomes "9."

Further, although in the above-described both embodiments, both the excitation light and the stimulation light are set as the structured illumination (structured illumination of the spatial frequency K), the excitation light out of the excitation light and the stimulation light may be set as uniform illumination (structured illumination of the spatial frequency zero). However, in this case, it is necessary to increase the intensity of stimulation light as compared to the case where both the excitation light and the stimulation light are set as the structured illumination.

Further, although in the above-described both embodiments, there has been described a method of acquiring a plurality of modulated images different in direction of interference fringes in order to obtain a super-resolution effect over a plurality of directions of the sample 5, as long as a modulated image is acquired with the use of structured illumination by means of incoherent two interference fringes deviating from each other by about 90° in terms of a direction, a substantially isotropic resolution can be obtained in an in-plane direction without acquiring modulated images with the use of structured illuminations in other directions. In this case, it is only necessary to use structured illumination by means of incoherent two excitation light interference fringes deviating from each other by about 90° in terms of a direction and structured illumination by means of incoherent two stimulation light interference fringes deviating from each other by about 90° in terms of a direction, and at the same time, make directions of the excitation light interference fringes coincide with directions of the stimulation light interference fringes.

Further, although it can be also considered that another optical process occurs simultaneously with a process of the stimulated emission, nonlinearity due to the optical process may be added to nonlinearity due to the stimulated emission to be utilized. When the stimulation light has absorption, for example, a process of ground state depletion (GSD: Ground State Depletion) occurs simultaneously with the process of stimulated emission, and further when the stimulation light has a wavelength corresponding to an energy difference between an excited state and a higher-order excited state, a process of excited state absorption occurs simultaneously with the process of stimulated emission. As above, even when the optical process other than the stimulated emission occurs, the above-described embodiments can be realized.

Operation and Effect of Embodiments

The structured illumination microscopic device (ST-SIM) of each of the above-described embodiments includes: a first spatial modulation unit (the pulsed laser light source 101, the optical parametric oscillator 103, the diffraction grating 13, the objective lens 6, and the like) that spatially modulate a fluorescent sample (the sample 5) using an excitation light having a sinusoidal illumination distribution of a spatial frequency K and having an optical frequency $\omega_1$ for shifting a fluorescent substance to an excitation level; a second spatial modulation unit (the pulsed laser light source 101, the optical parametric oscillator 104, the diffraction grating 13, the objective lens 6, and the like) that spatially modulates the fluorescent sample (sample 5) using a stimulation light having a sinusoidal illumination distribution of a spatial frequency K and having an optical frequency $\omega_2$ for shifting the excited fluorescent substance to a base level; and an imaging unit (the objective lens 6, the second objective lens 32, the imaging sensor 35, the controlling device 39, and the image storage-calculation device 40) that acquires, as a modulated image, an image (the modulated image $I_A$, the difference image $I_D$) of the fluorescent sample (sample 5) obtained by means of spontaneously emitted light (the fluorescence) generated by the fluorescent sample in accordance with the excitation light and the stimulation light.

Accordingly, the structured illumination microscopic device (ST-SIM) of each of the above-described embodiments can expand a super-resolution range (range of resoluble spatial frequency) as compared to the 2D-SIM using no stimulation light.

Furthermore, in the structured illumination microscopic device (ST-SIM) of each of the above-described embodiments, in addition to the excitation light illumination (spontaneous emission by means of the excitation light), the stimulation light illumination (stimulated emission by means of the stimulation light) is performed to generate a harmonic component by the nonlinearity in the process of stimulated emission, so that at least the intensity of excitation light does not have to be increased extremely like the NSIM.

Furthermore, in the structured illumination microscopic device (ST-SIM) of each of the above-described embodiments, as long as the intensity and the phase of the stimulation light are set appropriately, out of the spatial frequency components contained in the modulated image (modulated image $I_A$, difference image $I_D$), the high-frequency component of spatial frequency 3K or more is suppressed down to a noise level, resulting in that the demodulating calculation of the modulated image (modulated image $I_A$, difference image $I_D$) does not become complex.

Further, in the structured illumination microscopic device (ST-SIM) of the second embodiment, the modulated image (difference image $I_D$) is an image of the fluorescent sample obtained by means of a decrease in spontaneously emitted light caused by the stimulated emission light.

Further, in the structured illumination microscopic device (ST-SIM) of the second embodiment, the imaging unit takes a difference between an image of the fluorescent sample obtained by means of spontaneously emitted light generated in accordance with both the excitation light and the stimulation light and an image of the fluorescent sample obtained by means of spontaneously emitted light generated in accordance with only the excitation light, thereby acquiring the modulated image (difference image $I_D$).

Alternatively, in the structured illumination microscopic device (ST-SIM) of the second embodiment, the imaging unit detects a spontaneously emitted light generated in accordance with the excitation light and the stimulation light with an intensity modulated over a time direction in synchronization with the modulation, thereby acquiring the modulated image (difference image $I_D$).

Further, the structured illumination microscopic device (ST-SIM) of each of the above-described embodiments further includes a calculation unit (the image storage-calculation device 40) that mutually separates and extracts at least a modulated component modulated by a spatial frequency K, a modulated component modulated by a spatial frequency 2K, a modulated component modulated by a spatial component –K, a modulated component modulated by a spatial component −2K, and a modulated component modulated by a spatial frequency zerofrom modulated components contained in the modulated image.

[Others]

Further, the requirements of the above-described both embodiments can be appropriately combined. Further, there is a case where a part of the components is not used. Further, disclosures of all laid-open application publications and U.S. patents related to the devices and the like cited in the above-described respective embodiments and modified example are incorporated by reference as a part of this specification, as long as allowed by law.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illumination microscopic device, comprising:
   a first spatial modulator including
      a first optical converter that converts source light to excitation light having an optical frequency $\omega_1$ and for shifting a fluorescent substance to an excitation level,
      a brancher that branches the excitation light into plural excitation light beams, and
      an objective lens that forms the excitation light from the branched plural excitation light beams and spatially modulates a fluorescent sample, wherein the excitation light has a sinusoidal illumination distribution of a spatial frequency K;
   a second spatial modulator including
      a second optical converter that converts the source light to a stimulation light having an optical frequency $\omega_2$ and for shifting the fluorescent substance exciting to a base level,
      the brancher, wherein the brancher branches the stimulation light into plural stimulation light beams, and
      the objective lens, wherein the objective lens forms the stimulation light from the branched plural stimulation light beams and spatially modulates the fluorescent sample, wherein the stimulation light has a sinusoidal illumination distribution of the spatial frequency K; and
      an imager that forms and obtains, via the objective lens, a modulated image of the fluorescent sample with spontaneously emitted light generated at the fluorescent sample in accordance with the excitation light and the stimulation light.

2. The structured illumination microscopic device according to claim 1, wherein
   the modulated image is an image of the fluorescent sample due to a decrease in spontaneously emitted light caused by a stimulated emission light.

3. The structured illumination microscopic device according to claim 2, wherein
   the imager obtains the modulated image by taking a difference between an image of the fluorescent sample with spontaneously emitted light generated in accordance with both the excitation light and the stimulation light and an image of the fluorescent sample with spontaneously emitted light generated in accordance with only the excitation light.

4. The structured illumination microscopic device according to claim 2, wherein
   the imager obtains the modulated image by detecting a spontaneously emitted light generated in accordance with the excitation light and the stimulation light with an intensity modulated over a time direction in synchronization with the modulation.

5. The structured illumination microscopic device according claim 1, further comprising:
   a calculator mutually separating and extracting at least a modulated component modulated by the spatial frequency K, a modulated component modulated by a spatial frequency 2K, a modulated component modulated by a spatial frequency −K, a modulated component modulated by a spatial frequency −2K, and a modulated component modulated by a spatial frequency zero from modulated components contained in the modulated image.

6. A structured illumination observation method, comprising:
   converting source light to excitation light having an optical frequency $\omega_1$ and for shifting a fluorescent substance to an excitation level;
   branching the excitation light into plural excitation light beams;
   forming the excitation light from the branched plural excitation light beams and spatially modulating a fluorescent sample, wherein the excitation light has a sinusoidal illumination distribution of a spatial frequency K;
   converting the source light to stimulation light having an optical frequency $\omega_2$ and for shifting the fluorescent substance exciting to a base level;
   branching the stimulation light into plural stimulation light beams;
   forming the stimulation light from the branched plural stimulation light beams and spatially modulating the fluorescent sample, wherein the stimulation light has a sinusoidal illumination distribution of the spatial frequency K; and
   forming and obtaining a modulated image of the fluorescent sample with spontaneously emitted light generated at the fluorescent sample in accordance with the excitation light and the stimulation light.

* * * * *